United States Patent [19]

Axén et al.

[11] Patent Number: 4,469,796

[45] Date of Patent: Sep. 4, 1984

[54] ASSAYING METHODS INVOLVING BIOSPECIFIC AFFINITY REACTIONS

[75] Inventors: Rolf E. A. V. Axén, Bälinge; Sven O. H. Oscarsson, Örbyhus; Per H. G. Ponterius; Jan P. E. Carlsson, both of Upsala, all of Sweden

[73] Assignee: Pharmacia Diagnostics AB, Uppsala, Sweden

[21] Appl. No.: 260,684

[22] Filed: May 5, 1981

[30] Foreign Application Priority Data

May 19, 1980 [SE] Sweden .................................. 8003732

[51] Int. Cl.³ ............................................. G01N 33/50
[52] U.S. Cl. .................................. 436/518; 436/513; 436/529; 436/532; 436/535; 436/538; 436/540; 436/541; 436/542; 436/824; 436/827; 436/828; 435/7; 435/178; 435/181; 435/182
[58] Field of Search .................... 435/7, 177, 178, 180, 435/181, 182, 179; 424/1, 8, 12; 23/230 B; 436/528, 529, 532, 535, 541, 542, 545, 546, 530, 531, 513, 824, 538, 540

[56] References Cited

U.S. PATENT DOCUMENTS

| 3,839,153 | 10/1974 | Schuurs et al. | 435/7 |
| 4,139,604 | 2/1979 | Gutcho et al. | 424/1 |
| 4,145,406 | 3/1979 | Schick et al. | 23/230 B |
| 4,149,003 | 4/1979 | Carlsson et al. | 260/112 R |
| 4,175,073 | 11/1979 | Carlsson et al. | 435/7 |
| 4,180,383 | 12/1979 | Johnson | 23/230 B |
| 4,231,999 | 11/1980 | Carlsson et al. | 435/7 |
| 4,232,119 | 11/1980 | Carlsson et al. | 435/7 |
| 4,272,506 | 1/1981 | Schwartzberg | 435/7 |

FOREIGN PATENT DOCUMENTS 2040935 9/1980 United Kingdom .

*Primary Examiner*—Esther M. Kepplinger
*Attorney, Agent, or Firm*—Fred Philpitt

[57] ABSTRACT

An improvement in assaying methods involving biospecific affinity reactions, in which there are used from 2 to 4 reactants, one of which, reactant (I), is labelled with at least one analytically indicatable atom or group and is soluble in the aqueous liquid in which the biospecific affinity reaction is carried out, the reactants forming, by means of biospecific reactions, a conjugate in which labelled reactant (I) is incorporated; and in which assaying methods the analytically indicatable atom or group is assayed in the conjugate and/or in labelled reactant (I), which is not bound to the conjugate. The conjugate that has been formed or labelled reactant (I) not bound to the conjugate is bound covalently to an insoluble carrier or to an insolubilizable carrier, which latter carrier is made insoluble after the covalent binding has been carried out, whereafter the assay of the analytically indicatable atom or group is carried out.

4 Claims, No Drawings

ASSAYING METHODS INVOLVING BIOSPECIFIC AFFINITY REACTIONS

The present invention relates to an improvement in assaying methods involving biospecific affinity reactions, in which there are used from 2 to 4 reactants, one of which, reactant (I), is labelled with at least one analytically indicatable atom or group and is soluble in the aqueous liquid in which the biospecific affinity reaction is carried out, the reactants forming, by means of biospecific affinity reactions, a conjugate in which labelled reactant (I) is incorporated, and in which assaying methods the analytically indicatable atom or group is assayed in the conjugate and/or in labelled reactant (I) not bound to the conjugate.

In assaying methods of the above mentioned type involving biospecific affinity reactions (for instance immunochemical reactions) a reactant (I) [for instance an immunochemical reactant (I)], which is labelled and is soluble in the aqueous liquid in the presence of which the reaction takes place, may be reacted with a reactant (II) which exhibits biospecific affinity to (I) [i.e. (II) is a counterpart of (I) and, for instance, (II) is an immunochemical reactant (II)] and, possibly, with a third reactant (III), which exhibits biospecific affinity to (I) and/or (II) [i.e. (III) is a counterpart of (I) and/or (II) and, for instance, (III) is an immunochemical reactant (III)], and possibly with a fourth reactant (IV), which exhibits biospecific affinity to one of the other reactants [i.e. (IV) is a counterpart of one of said other reactants (I), (II) and (III), for example (III), and (IV) is for example an immunochemical reactant (IV)] to the formation of a conjugate (or complex as it also is called) in which labelled reactant (I) is incorporated.

By "immunochemical reactant" is meant in this connection immunoglobulins (including modified immunoglobulins, e.g. aggregated, and fragments, e.g. Fab- or Fc-fragments), preferably antibodies, and antigens and haptens.

Examples of reactants (I) and reactants (II) [as well as reactants (III) and (IV)] which exhibit biospecific affinity to one another (i.e. they are counterparts of each other) are antigens (or haptens) and specific antibodies directed thereagainst. Other examples include (a) Protein A (from *S. aureus*) and fragments thereof, which can bind the Fc-part of immunoglobulins belonging to the IgG-class; (b) C1q, which can, for example, bind to heat aggregated IgG; (c) lectins (e.g. Concanavalin A) which, e.g. can bind to specific carbohydrate structures in for example, biopolymers; (d) enzyme inhibitors which can bind to their enzyme; (e) receptors and ligands; (f) physiologically or pharmaceutically active substances capable of binding to corresponding receptors. There are many other such examples of pairs of substances which exhibit biospecific affinity to one another within the biochemical field, e.g. biotin-avidin, intrinsic factor-vitamin B12, etc.

Examples of reactant (III) when such reactant is taking part in the reaction is an unlabelled reactant (I) for instance for competition with labelled reactant (I), or an antibody directed against antibody or antigen in an antigen-antibody-complex in which one of the components is labelled.

Also a fourth reactant (IV) can take part, for instance in the sequence antigen←antibody(A)←antibody(B)-→labelled antibody(A).

Many other pairs of reactants of biological origin may be mentioned, the interaction of which is used for assaying methods of the above mentioned type, the concentration of one of the participating unlabelled reactants being determined.

The statement as to the labelled reactant (I) being soluble in the aqueous liquid in whose presence the biospecific affinity reaction is carried out includes here and in the claims that it, for instance, may be colloidally dispersible in said liquid or in another way be present in the form of particles sufficiently small to keep themselves suspended in the liquid.

A large number of assay methods of the aforementioned basic type, primarily concerning immunochemical assay methods, are known to the art.

In order to enable the assay of the analytically indicatable atom or group in the conjugate or in the labelled reactant (I) which is not bound to the conjugate a partition of said conjugate and said labelled reactant (I) which is not bound to the conjugate is carried out, for instance by means of precipitation methods, chromatographic methods (such as gel filtration), or electrophoretic methods.

An example of such a precipitation method is the so-called double-antibody method in which an insoluble immunochemical conjugate is formed which can be separated from components remaining in the solution.

An example of chromatographic methods is the separation of formed soluble conjugate from free (i.e. not bound to the conjugate) labelled reactant (I) by means of gel permeation chromatography.

In recent years said partition has often been attained by one of the participating reactants [however, not the labelled reactant (I)] being bound to an insoluble polymer so that the conjugate formed by the biospecific reactions will be attached to the insoluble polymer and by reason of that can be separated from labelled reactant (I) which is not bound to the conjugate but is present in solution. According to one group of such methods, there is used water-insoluble polymer material to which is bound an antibody or an antigen, for example a polypeptide-containing antigen or some other counterpart. Thus, it is known from, for example, British Patent Specification Nos. 1,192,784, 1,248,764 and 1,248,765 and Biochem. Biophys. Acta 130 (1966) page 257, and Radio-immunoassay Methods (Editors: K. E. Kirkham and W. M. Hunter, Churchil Livingstone, London 1971) e.g. pages 405–412 of the article "Solid Phase Antigen Antibody Systems" by L. Wide, to use a water-soluble polymer material to which an antibody or an antigen is bound by bonds of a covalent nature. Further, the U.S. Pat. No. 3,646,346 teaches an immunochemical assay method in which there is used antibodies absorbed on the inner surface of a plastics test tube.

It is also known, when carrying out the immunochemical and analogous assay methods in question, that one of the reactants [reactant (I)] involved in the assay method is labelled with an analytically indicatable atom or group, e.g. with a radioactive atom or group, a fluorescent, luminescent or chromophoric group, or an enzymatically active group or an enzyme inhibitor group or a coenzyme group.

The labelling of the reactant (I) (e.g. an antigen, an antibody etc.) with an analytically indicatable atom or group is nowadays well known, and well established techniques herefor are generally known. In this connection it is known that the label can be directly bound to the reactant (I) or that a bridge is introduced between the reactant (I) and the label.

A large number of variants of such assay methods (including immunochemical assay methods as well as analogous assay methods utilizing other reactants than immunochemical reactants which reactants have biospecific affinity to each other) in which there is used a labelled reactant, such as a labelled antigen, a labelled hapten, a labelled antibody or labelled protein A are described in the literature. (See for example the aforementioned references). Thus, for example (a) antibodies can be reacted with antigen in a sample and with labelled antigen or (b) antibodies can be reacted with antigen in a sample in a manner such that the antigen is bound to the antibody, whereafter there is added labelled antibody which binds to the bound antigen, or (c) antigen is reacted with antibody in a sample in a manner such that the antibody binds to the antigen, whereafter there is added labelled antigen which binds to the bound antibody, or (d) antigen is reacted with antibody in a sample in a manner such that the antibody binds to the antigen, whereafter there are added labelled antibodies directed against the first-mentioned antibodies and binding thereto, or (e) an antigen in a sample is reacted with a labelled antibody, or (f) an antibody in a sample is reacted with a labelled hapten or antigen.

The antibodies may belong to one or more immunoglobulin classes. What has been said concerning assay methods involving antigens and antibodies also applies to analogous assay methods involving other reactants than antigens and antibodies.

It is also well known that such assays are preferably carried out in the presence of an aqueous liquid, e.g. a buffer solution having a suitable pH and ionic strength.

In case of the quantitative assay of one of the reactants it is also well known to use varying known amounts of this reactant in order to establish standard curves which are then used for the determination of unknown amounts of said reactant.

Among the known methods, those using an insoluble polymer carrier for one of the reactants afford the definite advantage over the other methods whereby separation or partitioning of conjugate and labelled reactant (I) not bound to the conjugate may be achieved in a considerably simpler and more accurate fashion, whereas a considerable disadvantage is that when one of the participating reactants is bound to an insoluble carrier, the rate at which the biospecific affinity reaction proceeds is considerably slower than in the case when the reaction is carried out completely in solution.

Consequently, an object of the present invention is to provide a method which combines the advantages obtained with the presence of insoluble carrier material in the separation process with the advantages obtained by carrying out the biospecific affinity reactions in solution.

According to the present invention this combination of advantages is attained by a method which is characterized in that, after the formation of the conjugate, the formed conjugate or labelled reactant (I) not bound to the conjugate is bound covalently to an insoluble carrier or to an insolubilizable carrier, which latter is made insoluble after the covalent binding has been carried out, whereafter the assay of the analytically indicatable atom or group is carried out.

When binding one of the two components, the conjugate and the labelled reactant (I) not bound to the conjugate, it may be accepted that part of the other one of these components is also bound. What is essential is solely that one of the two components is bound to a definitely greater extent than the other. However, the accuracy of the method increases with an increasing difference in the extent to which the two aforementioned components are bound.

According to a preferred embodiment of the method according to the invention, there is used a carrier and an unlabelled reactant incorporated in the conjugate, which carrier and reactant each exhibit a respective type of reactive group, whereat said reactive groups are of the kind capable of reacting with one another to form a covalent bond between the carrier and said reactant, and whereat none of the reactive groups is present in any other of the reactants incorporated in the conjugate and whereat the unlabelled reactant does not compete with labelled reactant (I).

Due to the fact that a great number of reactive groups can be introduced into the carrier, a rapid and extensive binding of the conjugate to the carrier can be achieved by means of this embodiment.

Particularly preferred in this case is the use of a carrier which exhibits pyridyl disulphide groups and an unlabelled reactant, which is incorporated in the conjugate and does not compete with labelled reactant (I) and which exhibits SH-groups or vice versa, which groups can react with each other in a thiol-disulphide exchange reaction.

Pyridyl disulphide groups suitable for thiol-disulphide exchange reactions are those whose reduced form is of a low S-nucleophilicity due to resonance stabilization or thiol-thion-tautomerism, for instance 2-pyridyl, 5-nitro-2-pyridyl and 4-pyridyl.

The carrier may be a polymer which is insoluble or soluble in aqueous liquids. The polymer can be prepared synthetically or can be of natural origin and be provided with groups of the formula —SH, which groups are then transformed into pyridyl disulphide groups. It can also be of organic or partly inorganic nature. Particularly important groups of polymers in this connection are HS-groups-containing derivatives of such biopolymers as polysaccharides, proteins and polypeptides. The polymer can be cross-linked to a water-insoluble network, which, however, can be swellable in water. Examples of water-insoluble polymers are HS-groups-containing derivatives of agarose, cross-linked dextran or cross-linked starch (e.g. cross-linked with epichlorohydrin to the formation of an insoluble gel), cellulose or other polysaccharides, insoluble in water, or glass. HS-groups-containing derivatives of dextran, starch or other water-soluble polysaccharides may be mentioned as examples of water-soluble polymers. Other examples of polymers in this connection are native or modified soluble or insoluble proteins or polypeptides, which are inert against the biospecific affinity reaction system and exhibit free HS-groups. In many cases it is to advantage to use HS-groups-containing derivatives of polymer substances which are water-insoluble but swellable in water, e.g. such substances as cross-linked polymer substances containing hydrophilic groups such as hydroxyl groups.

There are many examples of polymer substances containing HS-groups. For instance, such a polymer is described in Acta Chem. Scand. Vol. 17 (1963), pp 2610–2621. Furthermore, some such polymers containing free HS-groups or pyridyl disulphide groups are commercially available. Examples thereof are copolymers of acrylamide containing the group

(Enzacryl ®Polythiol, Koch-Light Laboratories Ltd. England) and glass substituted with the group

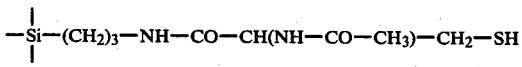

(Corning Thiol CPG, Corning Glass Co., USA).

Other examples include agarose substituted with the group —O—CH$_2$.CH(OH).CH$_2$—SH and agarose substituted with 2-pyridyl disulphide groups over bridges obtained by means of glutathione, which are commercially available (Thiopropyl-Sepharose ®6B and Activated Thiol-Sepharose ®4B from Pharmacia Fine Chemicals AB, Uppsala, Sweden).

In the polymeric carrier materials the HS-groups can be bound to a carbon atom situated in a polymer chain in the polymeric basic framework. Preferably, however, polymers are chosen wherein the HS-group is bound to a carbon atom which is present in a group which projects from a polymer chain in the polymeric basic framework and consequently is more accessible. The carbon atom to which the HS-group is bound can be present in an aliphatic or aromatic group in the polymer and is preferably in turn directly bound to at least one carbon atom.

The remaining bonds of the first-mentioned carbon atom are preferably saturated with hydrogen atoms. Preferably HS-groups are chosen which are present in the group —CH$_2$—SH or in a group

wherein the carbon atom is located in an aromatic ring such as a benzene ring. The polymer thus preferably contains at least one group of the formula

wherein one of the remaining bonds of the carbon atom passes to another carbon atom and the remaining bonds pass to carbon and/or hydrogen. What has been stated above as regards the binding of the HS-group to a carbon atom in the polymeric substance is also applicable to the pyridyl disulphide group.

A basic polymer, which does not contain HS-groups, can be made to exhibit such groups by thiolation in a manner known per se, for instance in the case of hydroxyl group containing polymers by amination and subsequent reaction with a thiolating agent such as a thiolimidate or N-acetylhomocystein thiollactone or alternatively by reaction of the hydroxyl group containing polymer with a 1-halo-2,3-epoxy-propane to the corresponding halohydroxypropyl derivative, which is reacted with Na$_2$S$_2$O$_3$ to form the corresponding mercaptohydroxypropyl derivative.

The pyridyl disulphide derivatives can be prepared by reacting an HS-group-containing polymeric substance according to the above with the appropriate dipyridyl disulphide or by reacting an amino group-containing polymeric substance in a corresponding fashion as is shown below for the introduction of a pyridyl disulphide structure in one of the reactants participating in the biospecific affinity reaction or reactions.

A favourable method for the introduction of one or more SH-groups, alternatively one or more pyridyl disulphide groups, suitable for thiol-disulphide exchange, into a reactant participating in biospecific affinity reactions of the types used in the present invention has been described in detail in, for instance, U.S. Pat. No. 4,149,003 and German "Offenlegungsschriften" Nos. 2,808,476 and 2,808,515. In these methods a reagent of the formula

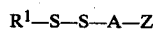

is used, wherein R$^1$ is 2-pyridyl, 5-nitro-2-pyridyl or 4-pyridyl, A is a hydrocarbon residue of 1 to 10 carbon atoms, preferably 1 to 6 carbon atoms, and Z is a group

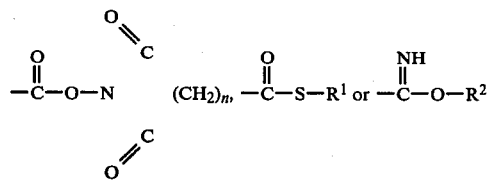

or acid addition salts of the last mentioned group, where n is 2 or 3, R$^1$ has the same significance as R$^1$ above and is equal thereto and R$^2$ is methyl or ethyl. This reagent reacts with an amino group of the reactant participating in the affinity reaction, a derivative being formed which, for instance, when the reagent is N-succinimidyl-3-(2-pyridyldithio)-propionate, exhibits groups of the formula

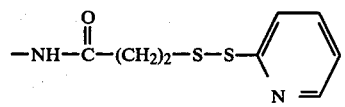

wherein —NH— constitutes the residue of said amino group of the reactant. In this derivative the disulphide bond may be split by treatment with a reducing agent such as dithiothreitol to form groups having the formula

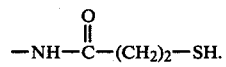

The conditions for both of these reactions have been disclosed in more detail in the above mentioned patent literature.

The reaction between conjugate and carrier is carried out under conditions commonly used for thiol-disulphide reactions, for instance in an aqueous medium at pH 2 to 8 and a temperature of from 15° to 30° C.

It is also possible to utilize this combination of reactive groups in the case of a water-soluble carrier, which is made insoluble after the covalent binding of the conjugate to the carrier has been carried out. In this case a water-soluble polymer containing pyridyl disulphide groups is used as carrier and an unlabelled reactant, which exhibits HS-groups and does not compete with labelled reactant (I) is incorporated in the conjugate, said HS-groups reacting with the pyridyl disulphide groups of the carrier in a thiol-disulphide exchange reaction to couple the conjugate and carrier together over an —S—S-bridge. The number of pyridyl disulphide groups is in this case chosen in such a way as to be in considerable excess in relation to the HS-groups of the conjugate. Subsequent to this coupling of the conjugate to the carrier, part of the pyridyl disulphide groups remaining in the carrier is transformed into HS-groups, by treatment with a reducing agent such as dithiothreitol. As a result of a reaction between the HS-groups thus formed and the remaining pyridyl disulphide groups, the carrier molecules are polymerized to form an insoluble product.

The thiol group (—SH) is a so-called soft nucleophile and the pyridyl disulphide structure is a so-called soft electrophile. In the reaction with a thiol group to produce a covalent bond between the carrier and unlabelled reactant incorporated in the conjugate, the pyridyl disulphide structure according to the above may be replaced with any other soft electrophile, such as, for instance, the maleimide structure

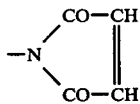

or the structure phenyl-HgCl.

On the other hand, a reaction between a so-called hard nucleophile and a so-called hard electrophile may also be used in order to effect the binding of the conjugate or reactant (I) not bound to the conjugate to the carrier, but in order to obtain the necessary separation effect a discriminatory condition must be enforced thereupon, since hard nucleophiles such as the $NH_2$-group usually occur in all the reactants participating in the affinity reactions of the assay methods and in a great number of other substances in the sample as well.

According to one embodiment of the method according to the invention applicable also in the case when the reactive groups are a hard nucleophile and a hard electrophile, the insoluble carrier used is one which exhibits a molecular network of such a mesh size that labelled reactant (I), which is not bound to the conjugate, and the conjugate differ considerably in their ability to penetrate the network, whereat the labelled reactant (I) and the network of the carrier exhibit reactive groups capable of reacting with each other to form a covalent bond between the labelled reactant (I) and the carrier.

Examples of such insoluble carriers exhibiting such molecular networks are polymeric gel filtration materials, such as agarose, cross-linked polysaccharides and cross-linked polyacrylamides with exclusion limits adjusted to exclude the conjugate in each individual case. Structures of a hard electrophile nature, such as imidocarbonate, oxirane, carbonate and chlorotriazine structures, may be introduced in a conventional manner. The introduction of these structures and their utilization for binding $NH_2$ or OH groups in biological substances belong to the classical methods within the field of assay of biologically active macromolecules and have been described thoroughly in the related literature.

When labelled reactant (I) does not contain $NH_2$ or OH, such as for instance in the case of steroids, the above mentioned hard electrophilic structures can be used as reactive groups on the carrier without it being necessary for said carrier to possess gel filtration properties (molecular sieving properties) with respect to the conjugate and labelled reactant (I).

The invention will now be described in more detail by means of a number of working examples.

EXAMPLE 1

Quantitative determination of sheep-antihuman IgG (a) Introduction of 2-pyridyl disulphide structures on human IgG 30 μl of N-succinimidyl-3-(2-pyridyldithio)propionate (from Pharmacia Fine Chemicals AB, Uppsala, Sweden), 4 mM in ethanol, were added to 1 ml of human IgG, 2 mg/ml in 0,1M Na-phosphate buffer pH 8.0. The reaction mixture was vigorously stirred during the actual addition process. The reaction was permitted to take place for 2 hrs at room temperature and pH 8.0, after which excess reagent was removed by desalting on a column 5.5×1.6 cm comprising particles of dextran cross-linked with epichlorohydrin (Sephadex ®G 25M from Pharmacia Fine Chemicals AB, Uppsala, Sweden).

(b) Labelling of sheep-antihuman IgG with $^{125}I$

A glass reaction tube was placed on an ice-bath. Added to the tube were
1. 10 μl of sheep-antihuman IgG, 4.5 mg/ml in 0.1M Na-phosphate buffer, pH 7.5;
2. 40 μl of 0.2M Na-phosphate buffer, pH 7.0, containing 0.02% by weight $NaN_3$;
3. 100 μl of 1.5 mM chloramine-T and 0.72 μl of Na $^{125}I$, 504.5 mCi/ml.

The mixture was allowed to react for 2 minutes at pH 7.0, whereafter the reaction was stopped by the addition of 20 μl of 0.1M $Na_2S_2O_3$ and 50 μl of 0.1M KI.

The reaction mixture was desalted on a column 0.9×15 cm containing particles of dextran cross-linked with epichlorohydrin (Sephadex ®G 25 coarse linked with epichlorohydrin (Sephadex ®G 25 coarse from Pharmacia Fine Chemicals AB, Uppsala, Sweden), which had been preprepared by applying 1 ml of 1% by weight bovine serum albumin (BSA) and equilibrating with 0.05M Na-phosphate buffer, pH 7.4, containing 0.05% by volume polyoxyethylene sorbitan monolaurate (Tween ®20); 0.02% by weight $NaN_3$; 0.05M $Na_2S_2O_3$.

Fractions of 0.5 ml were taken out. Fractions 2 to 6 were pooled and diluted five times in 0.05M phosphate buffer pH 7.4. The obtained solution was calculated to contain about 3 μg/ml with respect to sheep-antihuman IgG $^{125}I$.

(c) Preparation of thiol-substituted agarose 1 g of freeze-dried material consisting of agarose substituted with 2-pyridyl disulphide groups over bridges obtained by means of glutathione (Activated Thiol Sepharose ®4B from Pharmacia Fine Chemicals AB, Uppsala, Sweden) were allowed to swell for 15 minutes in 20 ml of 0.05M Na-phosphate buffer, pH 7.0. The gel was then washed first with 5×20 ml of distilled water and finally with 2×20 ml of 0.05M Na-phosphate buffer, pH 7.0. The washed gel was suspended in 20 ml of 0.05M Na-phosphate buffer, pH 7.0. For reduction purposes 0.25 ml of 50 mM dithiotreitol/ml gel suspension was added. The reduction was allowed to proceed for 60 minutes at pH 7.0 at room temperature. The gel was washed on a glass filter first with 5×20 ml of distilled water and finally with 100 ml of 0.05M Na-phosphate buffer.

(d) Pretreatment of horse serum 5 g of freeze-dried material consisting of agarose substituted with thiopropyl groups (Thiopropyl Sepharose®6B from Pharmacia Fine Chemicals AB, Uppsala, Sweden) were allowed to swell for 15 minutes in 20 ml of 0.05M Na-phosphate buffer, pH 7.0. The gel was washed according to the procedure described under (c) above. The washed gel was suspended in 20 ml of 0,05M Na-phosphate buffer, pH 7.0.

The above gel suspension was added to horse serum (from Phadebas®IgE-PRIST-kit from Pharmacia Diagnostics AB, Uppsala, Sweden) in a concentration of 1 ml suspension per ml horse serum.

The mixture was reacted for 2 hrs at room temperature, whereafter the gel was centrifuged down and the supernatant consisting of horse serum was drawn off by suction and recovered.

(e) Determination of sheep-antihuman IgG

To each of four tubes there were added 100 μl of sheep-antihuman IgG having the following concentrations: $1 \cdot 10^{-8}$M, $1 \cdot 10^{-9}$M, $1 \cdot 10^{-10}$M and $1 \cdot 10^{-11}$M, respectively. The dilution was carried out in horse serum treated in accordance with (d) above. 100 μl of $1.9 \cdot 10^{-9}$M sheep-antihuman-IgG $^{125}$I (from (b) above) and 100 μl of $1.9 \cdot 10^{-9}$M human-IgG-pyridyl disulphide (from (a) above) were then added. The reaction was allowed to continue for 3 hrs at room temperature on a vibrating table, whereafter 600 μl of 0.05M Na-phosphate buffer, pH 7.0, and 100 μl of reduced Activated Thiol Sepharose®4B (from (c) above) were added. The reaction was then allowed to continue for a further 2 hrs on a vibrating table at room temperature, whereafter the gel suspension was centrifuged and the supernatant was drawn off by suction. 2.5 ml of 0.5M NaCl-solution containing 0.5% by volume Tween®20 were added. The gel suspension was centrifuged down to the bottom of the tube and the supernatant was drawn off by suction. Subsequent to this washing procedure the radioactivity bound to the polymer was recorded with the aid of a counter.

The results are reproduced in Table I below.

TABLE I

| Sheep-antihuman IgG concentration M | Inhibation of sheep-anti-human-IgG-$^{125}$I uptake on polymer/total sheep-antihuman-IgG $^{125}$I added % (compared with blanks) |
|---|---|
| $1 \cdot 10^{-8}$ | 90.7 |
| $1 \cdot 10^{-9}$ | 33.6 |
| $1 \cdot 10^{-10}$ | 1.4 |
| $1 \cdot 10^{-11}$ | 0 |

EXAMPLE 2

Quantitative determination of sheep-antihuman IgG (a) Preparation of sheep-antihuman IgG-α-amylase derivative 4 mg of α-amylase (Bacterial Type II A from Sigma Chemical Company, St. Louis, Mo., USA) were dissolved in 1 ml of 0.1M Na-phosphate buffer, pH 7.0. 10 μl of N-succinimidyl-3-(2-pyridyldithio)-propionate (from Pharmacia Fine Chemicals AB, Uppsala, Sweden), 25 mM in 99.5% ethanol, were added while stirring vigorously. The reaction continued for 60 minutes at pH 7.0 at room temperature. Excess reagent was removed by desalting on a column 5.5×1.6 cm comprising particles of dextran cross-linked with epichlorohydrin (Sephadex ® G 25M from Pharmacia Fine Chemicals AB, Uppsala, Sweden).

3.8 mg of sheep-antihuman IgG (immunosorbentpurified in the manner shown below) were dissolved in 1 ml of 0.1M Na-phosphate buffer, pH 7.0. 10 μl of N-succinimidyl-3-(2-pyridyldithio)-propionate, 25 mM in 99.5% ethanol, were added while stirring vigorously. The reaction continued for 60 minutes at pH 7.0 at room temperature. Excess reagent was removed by desalting on a column 5.5×1.6 cm comprising Sephadex®G 25M.

1 ml of the above obtained α-amylase pyridyl disulphide preparation, $9.2 \cdot 10^{-6}$M, was reduced by the addition of 0.1 ml of 50 mM dithiothreitol, pH 7.0 (from Sigma Chemical Company, St. Louis, Mo., USA). The reduction was allowed to take place at room temperature for 30 minutes. Excess reagent was removed by desalting on a column 5.5×1.6 cm comprising Sephadex®G 25M.

1 ml of thiolated α-amylase preparation thus obtained, $8.3 \cdot 10^{-6}$M, was added to 0.5 ml of the above obtained sheep-antihuman-IgG-pyridyl disulphide, $8.6 \cdot 10^{-6}$M, while stirring the reaction mixture vigorously. The reaction continued at room temperature for 17 hrs at pH 7.0.

The immunosorbent-purification of sheep-antihuman IgG was carried out in the following manner:

10 g of CNBr-activated Sepharose®4B (from Pharmacia Fine Chemicals AB, Uppsala, Sweden) were permitted to swell for 15 minutes in $1 \cdot 10^{-3}$M HCl and then washed on a glass filter with 10×100 ml of $1 \cdot 10^{-3}$M HCl. The gel was then drained to dryness by suction on the filter, whereafter 100 ml of 0.1M NaHCO$_3$ containing 0.5M NaCl were added. After 15 minutes, 100 mg of human IgG were added. The reaction was allowed to proceed for 17 hrs at +4° C. Excess liquid was drawn off by suction on a glass filter and the gel was then washed with 500 ml of 0.1M tris(hydroxymethyl) aminomethane hydrochloride (Tris-HCl), pH 8.0 containing 1M NaCl. The gel was then washed further with 500 ml of 0.1M Na-acetate buffer, pH 4.0, containing 1M NaCl and finally with 500 ml of 0.1M Tris-HCl, pH 8.0, containing 1M NaCl. A column, 2×70 cm, was packed with the above gel and 400 ml of 0.1M Tris-HCl, pH 8.0, were pumped through the column.

10 ml of serum from sheep which had been immunized with human IgG were recirculated in the above column for one calendar day. Excess sheep serum was eluted out by washing with 0.1M Tris-HCl, pH 8.0, containing 0.02% by weight of NaN$_3$ until the eluate exhibited an extinction at A$_{280}$ nm of less than 0.2. Residual sheep serum was then eluted with 0.5M NaCl containing 0.02% by weight of NaN$_3$ until the eluate exhibited on an extinction at A$_{280}$ nm of less than 0.2. Finally specific sheep-antihuman IgG was eluted by eluting with 0.1M glycine-HCl, pH 3.0, containing 0.5M NaCl.

(b) Determination of sheep-antihuman IgG

To each of four tubes were added 100 μl sheep-antihuman IgG having the following concentrations: $6.8 \cdot 10^{-7}$M, $6.8 \cdot 10^{-8}$M, $6.8 \cdot 10^{-9}$M and $6.8 \cdot 10^{-10}$M (dilution was carried out in horse serum treated in accordance with Example 1(d)). 100 μl of $2 \cdot 10^{-7}$M sheep-antihuman IgG-α-amylase derivative (from (a) above) and 100 μl of $1 \cdot 10^{-7}$M human IgG-pyridyl-disulphide (prepared according to Example 1(a)) were then added. The reaction was allowed to proceed for 3 hrs at room temperature on a vibrating table, whereafter 600 μl of 0,05M Na-phosphate buffer, pH 7.0, and 100 μl of reduced Activated Thiol Sepharose ®4B (prepared according to Example 1(c)), were added. The reaction was then allowed to proceed for a further 2 hrs on a vibrating table at room temperature, whereafter the gel suspension was centrifuged down and the supernatant drawn off by suction.

2.5 ml of 0.5M NaCl-solution containing 0.5% by volume of Tween ®20 were then added.

The gel suspension was centrifuged down to the bottom of the tube and the supernatant was drawn off by suction. This washing procedure was repeated a further two times. 100 μl of 50 mM dithiothreitol were added to the reaction tube, to split off α-amylase from the immuno complex that is bound to the polymer. This splitting-off-reaction was allowed to proceed for 30 minutes at room temperature. 1000 μl of α-amylase substrate suspension comprising 1 tablet of coloured starch cross-linked with epichlorohydrin (Phadebas ®Amylase Test from Pharmacia Diagnostics AB) were then added to 4 ml of 0.05M Na-phosphate buffer, pH 7.0. The reaction was allowed to continue on a vibrating table at room temperature for 30 minutes, whereafter the reaction was stopped by the addition of 200 μl of 2M NaOH.

Subsequent to removing unreacted starch polymer by centrifugation in a reaction tube, the enzyme activity of the supernatant was registered by photometrically registering the light absorbance of the product at 619 nm.

The results are reproduced in Table II below.

TABLE II

| Concentration of sheep-antihuman IgG M | α-amylase activity bound to polymer at immuno complex/total α-amylase activity added % (compared to blanks) |
|---|---|
| $6.8 \cdot 10^{-7}$ | 36.9 |
| $6.8 \cdot 10^{-8}$ | 63.9 |
| $6.8 \cdot 10^{-9}$ | 100 |
| $6.8 \cdot 10^{-10}$ | 99.1 |

EXAMPLE 3

Quantitative determination of sheep-antihuman IgG with human IgG maleimidobenzamide and sheep-antihuman IgG $^{125}$I (a) Introduction of maleimidobenzamide structures into human IgG 10 μl of maleidobenzoyl-N-hydroxy succinimide ester (from Pierce, USA) dissolved to 16 mM in tetrahydrofuran were added to 1 ml of $1.4 \cdot 10^{-5}$M human IgG dissolved in 0.1M Na-phosphate buffer, pH 7.0, while stirring vigorously and were reacted for 2 hrs at room temperature.

Excess reagent was removed by desalting on a column 5.5×1.6 cm comprising Sephadex ®G 25M.

(b) Determination of sheep-antihuman IgG

To each of four tubes were added 100 μl of sheep-antihuman IgG of the following concentrations: $1.4 \cdot 10^{-8}$M, $1.4 \cdot 10^{-9}$M, $1.4 \cdot 10^{-10}$M and $1.4 \cdot 10^{-11}$M. The dilution of sheep-antihuman IgG was carried out in 0.1M Na-phosphate buffer, pH 7.0, containing 0.1% by volume of Tween ®20. Then 100 μl of $2.3 \cdot 10^{-9}$M sheep-antihuman IgG $^{125}$I (prepared according to Example 1(b)) and 100 μl of $1 \cdot 10^{-8}$M human IgG-maleimidobenzamide (from (a) above) were added. The reaction was allowed to proceed for 3 hrs at room temperature on a vibrating table, whereafter 600 μl of 0.5M Na-phosphate buffer, pH 7.0, and 100 μl of reduced Activated Thiol Sepharose ®4B (prepared according to Example 1(c)) were added. The reaction was then allowed to proceed for a further 2 hrs on a vibrating table at room temperature, whereafter the gel suspension was centrifuged and the supernatant drawn off by suction.

2.5 ml of 0.5M NaCl-solution containing 0.5% by volume of Tween ®20 were added. The gel suspension was centrifuged down to the bottom of the tube and the supernatant was drawn off by suction.

This washing procedure was repeated a further two times. Radioactivity bound to the polymer was registered in a γ-counter.

The results are represented in Table III below.

TABLE III

| Concentration of sheep-antihuman IgG M | Sheep-antihuman IgG $^{125}$I on gel Counts/0.5 minutes |
|---|---|
| $1.4 \cdot 10^{-8}$ | 17 449 |
| $1.4 \cdot 10^{-9}$ | 40 220 |
| $1.4 \cdot 10^{-10}$ | 53 519 |
| $1.4 \cdot 10^{-11}$ | 55 443 |

EXAMPLE 4

Quantitative determination of IgE by means of sheep-antihuman IgE-pyridyl disulphide and rabbit-antihuman IgE $^{125}$I (a) Introduction of 2-pyridyl disulphide structures into sheep-antihuman IgE 30 μl of N-succinimidyl-3-(2-pyridyl-dithio)propionate, 25 mM in 99.5% ethanol, were added to 1 ml of sheep-antihuman IgE, $8.58 \cdot 10^{-5}$M dissolved in 0.1 M Na-phosphate buffer, pH 7.0. The reaction mixture was stirred vigorously during the actual addition process and was allowed to react for 2 hrs at room temperature at pH 7.0, whereafter excess reagent was removed by desalting on a column 5.5×1.6 cm comprising Sephadex ®G 25M.

(b) Determination of IgE

To each of four tubes there were added 100 μl of IgE of the following concentrations: 200 U IgE/ml, 20 U IgE/ml, 2 U IgE/ml and 0.2 U IgE/ml. IgE was diluted in horse serum (from Phadebas ®PRIST from Pharmacia Diagnostics AB, Uppsala, Sweden). 100 μl of $8.58 \cdot 10^{-8}$M sheep-antihuman IgE-pyridyl disulphide (prepared according to (a) above) and 100 μl of 2.11·10⁻⁹M rabbit-antihuman IgE ¹²⁵I (prepared analogous to Example 1(b)) were then added. The reaction was allowed to proceed for 2 hrs at room temperature on a vibrating table, after which 100 μl of reduced Activated Thiol Sepharose ®4B (prepared according to Example 1(c)) were added. The reaction was then allowed to proceed for a further sixty minutes on a vibrating table at room temperature, whereafter the gel suspension was centrifuged and the supernatant drawn off by suction. 2.5 ml of 0.5M NaCl-solution containing 0.5% by volume of Tween ®20 were then added. The gel suspension was centrifuged down to the bottom of the tube and the supernatant was drawn off by suction. Subsequent to this washing procedure for the polymer, radioactivity bound to the polymer was registered in a counter.

The results are reproduced in Table IV below.

TABLE IV

| Concentration of IgE U/ml | Rabbit-antihuman IgE ¹²⁵I on gel Counts/0.5 minutes |
|---|---|
| 200 | 5 297 |
| 20 | 1 534 |
| 2 | 680 |
| 0.2 | 482 |
| 0 | 423 |

EXAMPLE 5

Quantitative determination of TSH with thiol-substituted rabbitIgG-antihuman TSH and TSH ¹²⁵I (a) Introduction of 2-pyridyl disulphide structures on rabbitIgG-antihuman TSH 16 μl of N-succinimidyl-3-(2-pyridyldithio)propionate, 5 mM in 99.5% ethanol, were added to 1 ml of rabbitIgG-antihuman TSH, 6.8·10⁻⁶M dissolved in 0.1M Na-phosphate buffer pH 7.5. The reaction mixture was stirred vigorously during the actual addition process and was reacted for 2 hrs at room temperature at pH 7.5, whereafter excess reagent was removed by desalting on a column 5.5×1.6 cm comprising Sephadex ®G 25M.

(b) Preparation of thiol-substituted rabbit-antihuman TSH

To 0.9 ml of rabbitIgG-antihuman TSH-pyridyl disulphide (from (a) above), 4·10⁻⁶M dissolved in 0.1M Na-phosphate buffer pH 7.5, there was added 0.1 ml of 58 mM dithiothreitol. The reaction was allowed to proceed for 30 minutes at pH 7.5 at room temperature, whereafter the reducing agent was removed by desalting on a column 5.5×1.6 cm comprising Sephadex ®G 25M.

(c) Determination of TSH

To each of six tubes there were added 50 μl of human TSH having the following concentrations: 50 μU/ml, 23 μU/ml, 11.5 μU/ml, 5.2 μU/ml, 2.4 μU/ml and 0 μU/ml. Dilution of TSH was carried out in plasma forming part of Phadebas ®TSH-test (from Pharmacia Diagnostics AB, Uppsala, Sweden).

50 μl of 1·10⁻⁸M thiol-substituted rabbitIgG-antihuman TSH (from (b) above) were then added. The reaction continued for 4 hrs at room temperature with the reaction mixture at rest. TSH ¹²⁵I 10 μCi/ml Phadebas ®TSH-test (from Pharmacia Diagnostics AB, Uppsala, Sweden) was then added.

After 2 hrs, 100 μl of Activated Thiol Sepharose ®4B, 20 mg of swollen gel/tube, were added. The reaction was allowed to proceed for 30 minutes on a vibrating table at room temperature. The gel suspension was then centrifuged and the supernatant was drawn off by suction. 2.5 ml of 0.5M NaCl-solution containing 0.5% by volume of Tween ®20 were then added. The gel suspension was centrifuged down and the supernatant siphoned off. After this washing procedure, the radioactivity bound to the polymer was registered in a counter.

The results are reproduced in Table V below.

TABLE V

| Concentration of human TSH μU/ml serum | TSH ¹²⁵I bound to polymer/total TSH ¹²⁵I added % (compared to blanks) |
|---|---|
| 50 | 38.7 |
| 23 | 59.0 |
| 11.5 | 75.5 |
| 5.4 | 85.5 |
| 2.3 | 92.6 |
| 0 | 100 |

EXAMPLE 6

Quantitative determination of nortriptyline by means of thiol-substituted sheepIgG-antinortriptyline and nortriptylin ¹²⁵I (a) Introduction of 2-pyridyl-disulphide structures on sheepIgG-antinortriptyline 50 μl of N-succinimidyl-3-(2-pyridyldithio)propionate, 4.7 mM in ethanol, were added to 1 ml of sheepIgG-antinortriptyline, 7.6·10⁻⁶M dissolved in 0.1M Na-phosphate buffer pH 8.0. The reaction mixture was stirred vigorously and allowed to react for 2 hrs at room temperature and pH 7.5. Excess reagent was removed by desalting on a column 5.5×1.6 cm comprising Swphadex ®G 25M.

(b) Preparation of thiol-substituted sheepIgG-antinortriptyline 0.1 ml of 58 mM dithiothreitol was added to 0.9 ml of sheepIgG-antinortriptyline-pyridyl disulphide (from (a) above), 7·10⁻⁶M dissolved in 0.1M Na-phosphate buffer pH 7.5. The reaction was allowed to proceed for 30 minutes at pH 7.5 and room temperature, whereafter the reducing agent was removed by desalting on a column 5.5×1.6 cm comprising Sephadex ®G 25M.

(c) Derivation of 3-(10,11-dihydro-5H-dibenzo[a,d]cyclohepten-5-ylidene)-N-(2-carboxypropionyl)-1-propane-amine 200 mg of 3-(10,11-dihydro-5H-dibenzo[a,d]cyclohepten-5-ylidene)-N-(2-carboxypropionyl)-1-propaneamine were dissolved in 5.7 ml of dry tetrahydrofuran. N₂ (dried over H₂SO₄) was led down into the vessel. The solution was chilled to −10° C. 79.9 μl of triethylamine and 74.8 μl of isobutyl chloroformate were then added. The mixture was stirred for about 15 minutes, whereafter a solution of 210.7 mg of histamine.2HCl and 319.3 μl of triethylamine in 11.5 ml of dimethyl-formamide was added. Stirring was continued for about 30 minutes at −10° C., whereafter the mixture was allowed to reach room temperature over night.

Insoluble substance was removed by suction, whereafter the filtrate was evaporated to a residue in the form of an oil. The oil was then treated with saturated NaHCO$_3$-solution. After extraction with EtOAc, the ethyl acetate phase was dried over Na$_2$SO$_4$ and evaporated. During this evaporation process 77.5 mg of colourless crystals precipitated out. M.p. 174°–176.5° C.

(d) Labelling of product obtained according to (c) with $^{125}$I

A glass reaction tube was placed on an ice bath. To the tube were added:

1. 40 μl of product obtained according to (c) dissolved to a content of 710 μg/ml in 40% by volume methanol;
2. 8 μl of Na $^{125}$I, 466.8 mCi/ml and
3. 50 μl of 1 mM chloramine-T.

The mixture was allowed to react for 2 minutes at pH 7.0, whereafter the reaction was stopped by the addition of 20 μl of 0.1M Na$_2$S$_2$O$_3$ and 50 μl of 0.1M KI.

The reaction mixture was desalted on a column 0.9×15 cm comprising Sephadex ®G 25 Superfine (from Pharmacia Fine Chemicals AB, Uppsala, Sweden). The buffer used for elution was 0.1M tris(hydroxymethyl)aminomethane-HCl buffer (Tris-HCl-buffer), pH 7.4, containing 0.5M NaCl.

(e) Determination of nortriptyline

To each of six tubes there were added 50 μl of nortriptyline having the following concentrations: 2.5 ng/ml; 60 ng/ml; 150 ng/ml; 600 ng/ml and 1000 ng/ml. The dilution of nortriptyline was carried out in nortriptyline-free serum.

50 μl of $2.5 \cdot 10^{-7}$M thiol-substituted sheepIgG-antinortriptyline (from (b) above) and 50 μl of $4 \cdot 10^{-10}$M product labelled according to (d) above were then added. These two substances were diluted in 0.1M Tris-HCl buffer pH 7.4 containing $1.0 \cdot 10^{-3}$M quinine and 0.05% by weight of sodium azide. After incubation for 30 minutes at room temperature without shaking, 100 μl of Activated Thiol Sepharose ®4B, 20 mg of swollen gel/tube were added. The reaction was allowed to proceed at room temperature without shaking for 10 minutes. The gel suspension was then centrifuged and the supernatant siphoned off. 2.5 ml of 0.9% by weight NaCl-solution were then added. The gel suspension was centrifuged down and the supernatant was drawn off by suction. This washing procedure was repeated a further two times. The radioactivity bound to the polymer was then registered by means of a counter.

The results are reproduced in Table VI below.

TABLE VI

| Nortriptyline ng/ml | Nortriptyline $^{125}$I bound to polymer/total nortriptyline $^{125}$I added % (compared with blanks) |
|---|---|
| 1000 | 21.0 |
| 600 | 29.0 |
| 300 | 38.5 |
| 150 | 51.2 |
| 60 | 67.4 |
| 25 | 78.0 |

EXAMPLE 7

Quantitative determination of IgE in serum

IgE standard serum was obtained by diluting a patient serum in horse serum in the following concentrations: 4000, 400, 100, 40 and 10 I.U. (International Units) IgE/ml.

100 μl of IgE-standard and 100 μl of $^{125}$I-labelled IgE (about 40 000 cpm) (from Phadebas ®RIST-IgE kit from Pharmacia Diagnostics AB, Uppsala, Sweden) were mixed with 100 μl of anti-IgE (antibodies against the Fc-part of IgE (anti-D$_2$) prepared according to Example 2 of British Patent Specification No. 1 248 764) diluted in 0.1M phosphate buffer pH 7.4 to 1 μg/ml. The competitive reaction to these antibodies was carried out for 15 hrs while shaking the tubes. 1 ml of 0.1M NaHCO$_3$ with CNBr-activated Sepharose ®4B was then added; 70 mg of freeze-dried material (about 250 μl gel) were used for each tube. The coupling reaction was allowed to proceed for 30 minutes while rotating the tubes and the solid phase was then washed with 0.3M NaCl containing 0.1% by volume of Tween ®20. After repeated washing and centrifugating the solid phase, its activity was measured in a gamma counter.

The results are reproduced in Table VII below.

TABLE VII

| Concentration of IgE I.U./ml | $^{125}$I-labelled IgE on gel Counts/minute |
|---|---|
| 4 000 | 13 475 |
| 400 | 10 377 |
| 100 | 4 579 |
| 40 | 3 097 |
| 10 | 2 846 |
| 0 | 2 596 |

EXAMPLE 8

Quantitative determination of digoxin in serum

Phadebas ® digoxin RIA (from Pharmacia Diagnostics AB, Uppsala, Sweden) was used.

100 μl of digoxin standard and 100 μl of $^{125}$I-labelled digoxin (about 40 000 cpm) were mixed with 100 μl of anti-digoxin prepared by precipitation with 18% Na$_2$SO$_4$. The concentration of the gammaglobulin fraction used was 18.5 μg/ml diluted in 0.1M phosphate buffer pH 7.4. The competitive reaction was then allowed to proceed for 1 hr, after which period CNBr-activated Sepharose ®4B was added in 1 ml of 0.1M NaHCO$_3$; 70 mg of freeze-dried material (∼250 μl gel) were used per tube. After the coupling reaction which lasted 30 minutes while the tubes were rotated, the solid phase was separated from the solution by means of centrifugation. In order to obviate the need of washing procedures, it was elected to determine the activity by taking the requisite measurements on the supernatant (500 μl).

The results are reproduced in Table VIII below.

TABLE VIII

| Concentration of digoxin nM | $^{125}$I-labelled digoxin in supernatant Counts/minute |
|---|---|
| 8 | 12 074 |
| 4 | 8 508 |
| 2 | 7 428 |
| 1 | 7 127 |
| 0.5 | 7 042 |
| 0 | 6 971 |

We claim:

1. In assaying methods involving biospecific affinity reactions, in which there are used from 2 to 4 reactants, one of which, reactant (I), is labelled with at least one analytically indicatable atom or group and is soluble in the aqueous liquid in which the biospecific affinity reaction is carried out, the reactants forming, by means of biospecific affinity reactions, a conjugate in which labelled reactant (I) is incorporated, and in which assaying methods the analytically indicatable atom or group is assayed in the conjugate and/or in labelled reactant (I) not bound to the conjugate, the improvement which comprises (a) binding, after the formation of the conjugate, the formed conjugate or labelled reactant (I) not bound to the conjugate convalently to an insoluble carrier or to an insolubilizable carrier, which latter is made insoluble after the covalent binding has been carried out, said carrier and said unlabelled reactant incorporated in the conjugate each exhibiting a respective type of reactive groups being of the kind capable of reacting with one another to form a covalent bond between the carrier and said reactant, and none of the reactive groups being present in any other of the reactants incorporated in the conjugate and the unlabelled reactant not competing with labelled reactant (I), and (b) then carrying out the assay of the analytically indicatable atom or group.

2. A method as claimed in claim 1, wherein there is used as said carrier one which exhibits pyridyl disulphide or SH-groups and as said unlabelled reactant one which is incorporated in the conjugate and does not compete with labelled reactant (I) and which exhibits SH-groups when the carrier exhibits pyridyl disulphide groups or pyridyl disulphide groups when the carrier exhibits SH-groups, which groups can react with each other in a thiol-disulphide exchange reaction.

3. A method as claimed in claim 1 wherein a soluble polymer containing pyridyl disulphide groups is used as the carrier, part of said groups being reduced to SH-groups after the conjugate or labelled reactant (I) not bound to the conjugate has been covalently bound to the carrier, thereby polymerizing the carrier molecules to an insoluble polymer by a reaction between formed SH-groups and residual pyridyl disulphide groups.

4. In assaying methods involving biospecific affinity reactions, in which there are used from 2 to 4 reactants, one of which, reactant (I), is labelled with at least one analytically indicatable atom or group and is soluble in the aqueous liquid in which the biospecific affinity reaction is carried out, the reactants forming, by means of biospecific affinity reactions, a conjugate in which labelled reactant (I) is incorporated, and in which assaying methods the analytically indicatable atom or group is assayed in the conjugate and/or in labelled reactant (I) not bound to the conjugate, the improvement which comprises (a) binding, after the formation of the conjugate, the labelled reactant (I) not bound to the conjugate covalently to an insoluble carrier exhibiting a molecule network of such mesh size that labelled reactant (I) not bound to the conjugate and the conjugate differ considerably in their ability to penetrate the network, the labelled reactant (I) and network of the carrier exhibiting reactive groups capable of reacting with each other to form a covalent bond between the labelled reactant (I) and the carrier, and (b) then carrying out the assay of the analytically incatable atom or group.

* * * * *